(12) United States Patent
Moore

(10) Patent No.: US 9,643,043 B1
(45) Date of Patent: May 9, 2017

(54) METHOD AND DEVICE FOR REBUILDING CORE STRENGTH IN A PATIENT

(71) Applicant: Debra S. Moore, Columbia, SC (US)

(72) Inventor: Debra S. Moore, Columbia, SC (US)

( * ) Notice: Subject to any disclaimer, the term of this patent is extended or adjusted under 35 U.S.C. 154(b) by 0 days.

(21) Appl. No.: 14/836,240

(22) Filed: Aug. 26, 2015

Related U.S. Application Data

(60) Provisional application No. 62/042,510, filed on Aug. 27, 2014.

(51) Int. Cl.
| | |
|---|---|
| *A63B 21/00* | (2006.01) |
| *A63B 21/28* | (2006.01) |
| *A63B 23/02* | (2006.01) |
| *A61H 1/02* | (2006.01) |

(52) U.S. Cl.
CPC .......... *A63B 21/28* (2013.01); *A63B 21/1469* (2013.01); *A63B 23/02* (2013.01); *A61H 1/02* (2013.01); *A61H 2201/16* (2013.01); *A61H 2201/1633* (2013.01); *A61H 2203/0456* (2013.01)

(58) Field of Classification Search
CPC .......... A63B 21/28; A63B 23/02; A61H 1/00; A61H 1/001; A61H 1/02; A61H 1/0274; A61H 1/0292; A61H 2201/16; A61H 2201/1635; A61H 2201/1638; A61H 2203/04; A61H 2203/0443; A61H 2203/0456
USPC .............................. 601/5, 23, 33; 1/5, 23, 33
See application file for complete search history.

(56) References Cited

U.S. PATENT DOCUMENTS

| | | | |
|---|---|---|---|
| 2,057,811 A | 10/1936 | Armstrong | |
| 3,129,940 A * | 4/1964 | Lauro ................... | A63B 21/28 273/451 |
| 4,169,591 A | 10/1979 | Douglas | |
| 4,304,402 A | 12/1981 | Ripp | |
| 4,644,595 A | 2/1987 | Daniel | |
| 4,852,873 A | 8/1989 | O'Donnell et al. | |

(Continued)

OTHER PUBLICATIONS

Jerrold S. Petrofsky, Ph.D.; Maria Cuneo, DPT; Russell Dial, DPT; Ashley K. Pawley; Jennifer Hill, BS; article entitled: Core Strengthening and Balance in the Geriatric Population from the Journal of Applied Research vol. 5, No. 3, 2005.

*Primary Examiner* — Loan H Thanh
*Assistant Examiner* — Megan Anderson
(74) *Attorney, Agent, or Firm* — Michael A. Mann; Nexsen Pruet, LLC

(57) ABSTRACT

A method with associated device for exercising core muscles of a patient who must maintain core strength or rebuild it from a very low level. The device has two handles separated by a transmission bar. A first handle is provided for the caregiver to hold, with both hands, and the opposing handle is provided for the patient to hold, again with both hands. The device enables the patient to pull herself from a supine position to a sitting position as the caregiver holds it stationery or, if the patient is lacking strength, to move the device slowly away from the patient. The caregiver can stand close to the bed corners and repeat the process to enable the patient to gain strength in the oblique muscles necessary to initiate rolling on the bed. The device, when used interactively with the patient, encourages the patient and provides feedback to the caregiver regarding the patient's fatigue level.

11 Claims, 5 Drawing Sheets

(56) References Cited

U.S. PATENT DOCUMENTS

| | | | |
|---|---|---|---|
| 5,941,799 A * | 8/1999 | Bergdorf | A63B 21/0455 |
| | | | 482/126 |
| 6,447,434 B1 * | 9/2002 | Waters | A63B 21/28 |
| | | | 482/140 |
| 6,966,872 B2 | 11/2005 | Eschenbach | |
| 7,004,893 B1 * | 2/2006 | Waters | A63B 21/28 |
| | | | 482/140 |
| 7,288,052 B1 | 10/2007 | Guillaume | |
| 7,601,109 B2 | 10/2009 | Roumayah | |
| 7,608,031 B2 | 10/2009 | Kerry | |
| 8,449,481 B2 * | 5/2013 | Rohde | A61B 17/42 |
| | | | 601/23 |
| 2005/0192169 A1 * | 9/2005 | Girgen | A61B 17/42 |
| | | | 482/139 |
| 2006/0189461 A1 | 8/2006 | Bishop | |
| 2007/0225134 A1 * | 9/2007 | Slattery | A63B 21/0004 |
| | | | 482/140 |
| 2010/0056350 A1 * | 3/2010 | Slattery | A63B 21/0004 |
| | | | 482/140 |
| 2012/0190517 A1 | 7/2012 | Scott | |
| 2016/0008653 A1 * | 1/2016 | Dipasquale | A63B 21/0728 |
| | | | 482/107 |

* cited by examiner

METHOD AND DEVICE FOR REBUILDING CORE STRENGTH IN A PATIENT

BACKGROUND

There is widespread and well-founded belief that exercise is vital to health. Some level of exercise is inevitable in everyday life for the vast majority of people. They walk, they lift objects, they climb stairs, they get in and out of cars, they stand up and they sit down.

However, from time to time, there are individuals who suffer an injury or illness so debilitating that they remain bedridden for extended periods of time, perhaps months, perhaps longer. While ill or injured, their muscles atrophy, perhaps to the point where they require assistance in raising themselves up or turning themselves. When movement itself becomes an issue, then a decline in health is inevitable and swift. Maintaining or restoring the ability of a chronically bedridden patient to move becomes a top priority.

SUMMARY OF THE INVENTION

This disclosure describes a device and exercises using the device to assist a bedridden patient in rebuilding and maintaining core and other muscles. The device used in these exercises has two spaced apart handles attached to a transmission bar. A first handle is provided for the caregiver to hold with both hands and an opposing handle for the patient to hold with both hands. The transmission bar is used by the caregiver to assist the patient in performing the exercises in accordance with the present method. The caregiver may be an occupational, physical, or speech therapist but may also be a relative, friend, nurse, or other person who has had a modicum of training in the use of the device with patients, particularly those who have lost almost all core strength.

In using the device, the caregiver stands at the foot of the patient's bed centered between its corners and holds the second end of the device while extending the first end toward the supine patient. The patient is instructed to grasp the extended end with both hands and to pull herself to a sitting position. The caregiver holds the device stationary, but, if the patient cannot pull herself up, will pull on the bar slowly and to the extent needed to help the patient pull herself to the sitting position. The caregiver will next instruct the patient to lower herself slowly to a supine position. This procedure may be repeated immediately the same day as tolerated by the patient or repeated later the same day or the next day to slowly build up core strength in the patient.

The caregiver may also take a step or two to one side of the center of the foot of the bed so that the patient will have to twist her core slightly using her oblique muscles. The patient in this position will attempt to pull herself from a supine to a sitting position while the caregiver holds the device stationary or pulls it backward slightly. The caregiver may then take one or two steps from the initial, centered position to the opposing side and repeat. In both positions for the caregiver, the patient will be asked to raise herself slowly from a supine to as close as she can to a sitting position and then to slowly lower herself to a supine position. The purpose of this exercising the oblique muscles is to strengthen the patient so that she can eventually roll in bed from side to side, or to prepare for standing up.

Patients who suffer from hemiplegia or who have undergone an arm amputation can benefit from the present device and its method of use with one hand.

In cases in which patients tend to become combative, the present device enables the therapist to maintain a safe distance, which allows the scope of exercises to be completed and a successful outcome to be more likely.

Core strengthening exercises are not the only exercises that are facilitated by using the present device. It may also be used in speech therapy. Laryngeal exercises such as pitch glides can be performed while strengthening the core muscles to increase safety in swallowing by improving subglottic pressure and the Bernoulli Effect in the wind pipe.

Use of the device for laryngeal exercise during core strengthening exercises increases resistance, such as when doing pitch glides, because it elevates the larynx and increases subglottic pressure which in turn increases the Bernoulli Effect in the wind pipe. Increasing resistance improves the patient's ability to control vocal modulation, intonation and inflection which promotes swallowing safety and reduces the incidence of phonation disorders. A speech therapist can use the present device and method for increasing vocal fold adduction, volume, and for voice production with vocalic sound production.

Use of the present device also improves larynx closure, important for breathing, sound production, and avoiding food aspiration, which is critical for patients who have difficulty swallowing or those suffering from dysphagia. Larynx closure can be exercised by having the patient cough while pulling and pushing on the device as a caregiver resists movement.

The present device is portable, inexpensive, light weight, easily stored in a narrow space, and easy to learn to use. The device is also easily cleaned for infection control. It can be used with multiple patients and in many settings such as acute care, home health, out-patient, post-acute care facilities, and skilled nursing homes that provide rehabilitation.

A feature of the disclosure is the method by which a caregiver can assist a chronically bed-ridden patient in rehabilitating core muscles. The device has opposing handles connected by a transmission bar, and is used by having the caregiver move to the foot of a bed between its two spaced-apart corners, grasping one of the device's two spaced-apart handles with both hands, extending the opposing handle of the device toward the patient so that the opposing handle is an arm's length away from the patient. The patient then by grasps the opposing handle with both hands and pulls, bending at the waste, while the caregiver resists movement of the device until the patient cannot pull closer to said opposing handle. Then, while the caregiver continues to provide resistance against movement of the device, the patient slowly lowers herself onto the bed.

Another aspect of the invention is that the caregiver can begin by moving to first one corner of the bed before extending the opposing end of the device to the patient for use and then repeating from the opposing corner of the bed to enable the patient to exercise her oblique muscles.

It is another feature of the invention that the caregiver may move away from the bed as the patient pulls on the opposing end of the device.

Still another feature of the invention is that the patient may perform vocal exercises while raising and lowering herself, such as laryngeal exercises, for example, pitch glides.

Another feature of the invention is a device for rehabilitation of a bedridden patient, comprising: a first handle, a second handle spaced apart from the first handle; and a transmission bar joined to the first and second handle. The transmission bar joins to the midpoint of the first and second handles, which handles are parallel to each other and perpendicular to the transmission bar.

Still another feature of the present disclosure is that the transmission bar is between 88 and 92 cm. long and the first and second handles are both between 26 and 31 cm. long, and the device itself is made of tubing.

It will be clear to those skilled in patient care, from a careful reading of the Detailed Description of Embodiments and accompanied by the drawings, that the present method has many other features and advantages.

BRIEF DESCRIPTION OF THE DRAWINGS

In the figures.

DETAILED DESCRIPTION OF PREFERRED EMBODIMENTS

The present method requires a caregiver and a device as described herein. The device is to be used by the caregiver and the patient in accordance with the present method. The term caregiver is not limited to professionals such as physical therapists, occupational therapists, nurses, nurses' aides, medical doctors, physician assistants, or hospitals orderlies, but also includes relatives, spouses, and friends who attempt to assist the particular patient.

The phrase bedridden means that the patient spends the majority of his or her time lying in bed except when being moved or turned by others and has been bedridden for a sufficient time to have experienced a loss of core muscle strength so that the patient needs assistance to sit up in bed so that the patient needs assistance to sit up in bed, or to roll left or right.

The term patient may not mean necessarily that the individual is undergoing treatment in a hospital, a convalescent home, a nursing home or a hospice facility but only means that the individual lying in a bed and has difficulty sitting up without assistance yet is willing to attempt to rehabilitate his or her core muscles with help from others.

The patient and the caregiver are human beings, and it is convenient in describing human beings to use pronouns. Accordingly, the use of a male or a female pronoun is used herein purely for simplicity of description and without regard to whether the patient is male or female, and it must be understood that the present device is intended for either male or female caregivers and patients.

Core muscles include the pelvic floor muscles, abdominis transversus, multifidus, internal and external obliques, rectus abdominis, erector spinae (sacrospinalis) especially the thoracis longissimus, the diaphragm, the latissimus dorsi, gluteus maximus, and trapezius. These muscles are all important to basic movement and some, such as the rectus abdominis and others are more important than others for sitting up. Restoring health begins by restoring these muscles to the point where the patient can begin to move herself safely.

Figure 1:
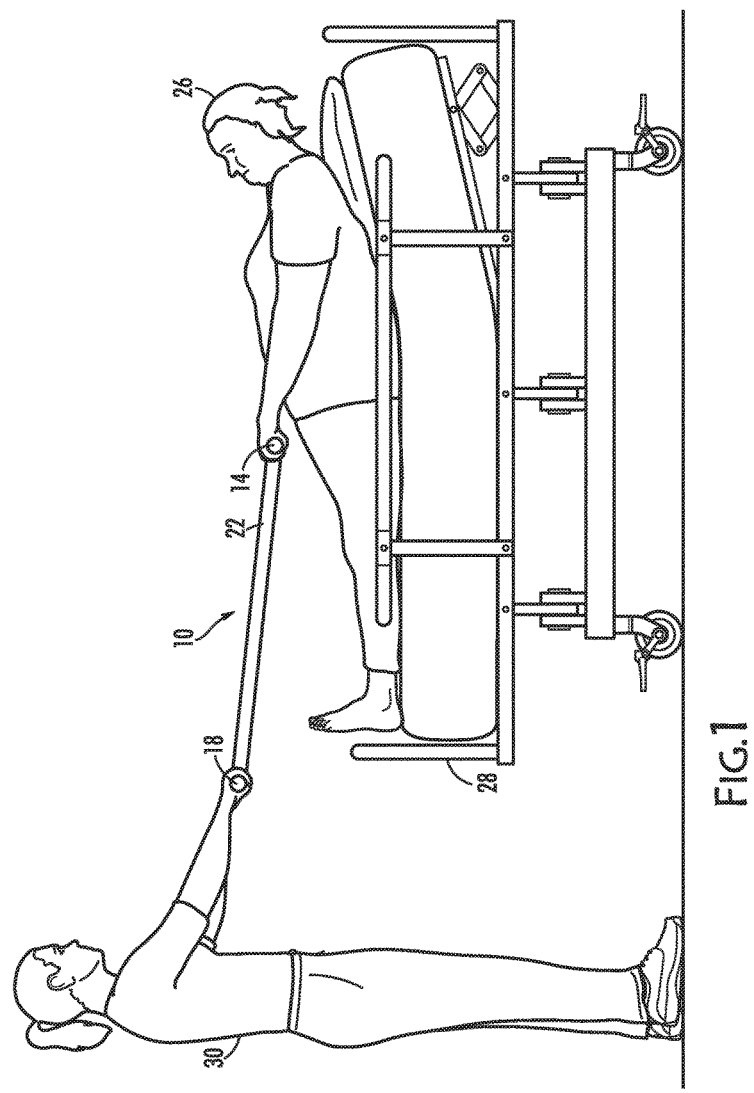
FIG. 1 shows the present method in use, in a side view of a patient lying on a bed, the caregiver standing at the foot of the patient's bed and with the transmission handle between them.
Figure 2:
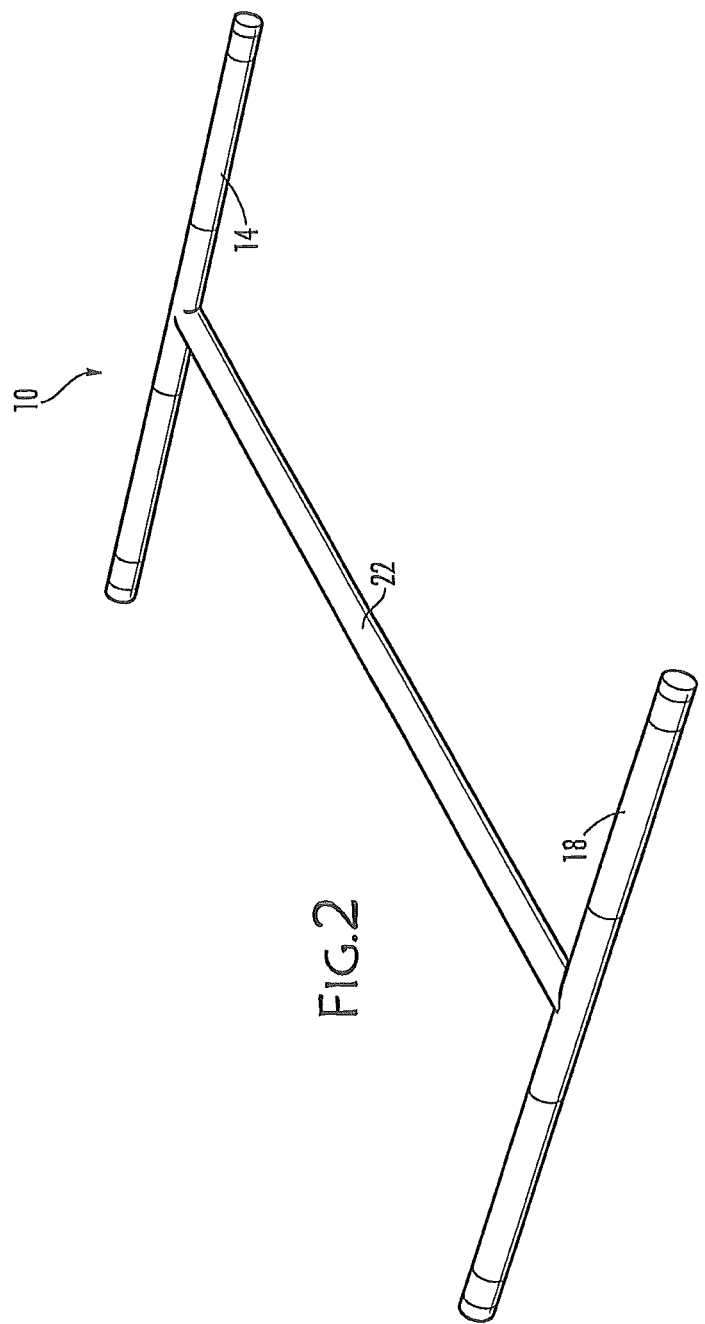
FIG. 2 is a perspective view of the device for use in the present method.
Figure 3:
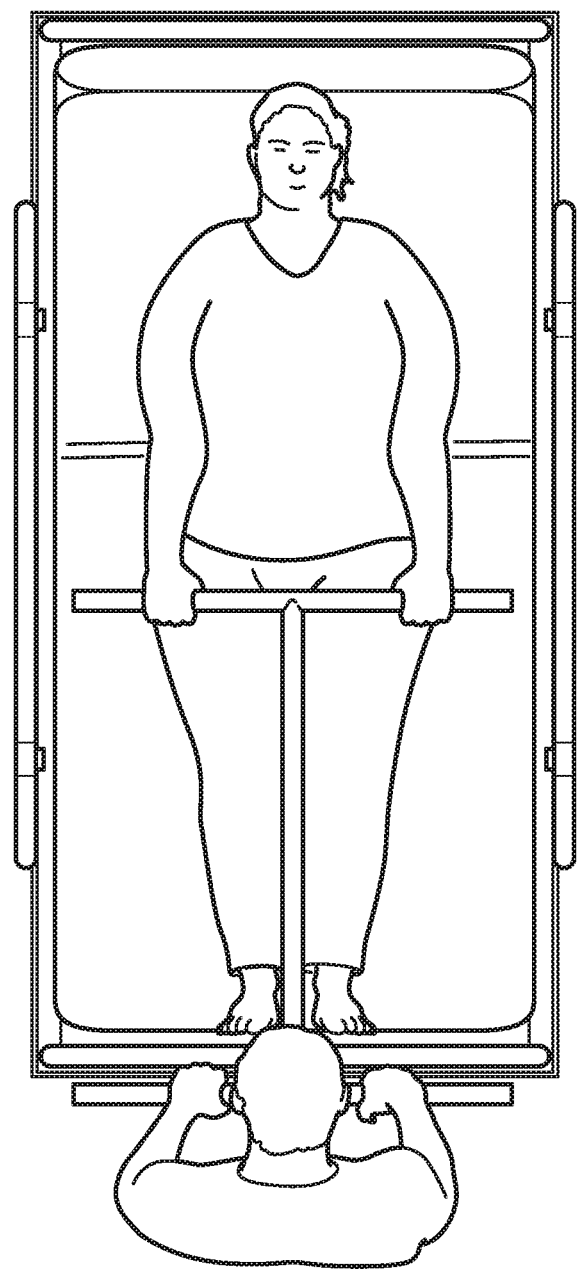
FIGS. 3, 4 and 5 are top views of a bedridden patient with a caregiver at the foot of the patient's bed, to the left of the foot, and to the right of the foot of the patient's bed holding the device by the first and second handles with the transmission bar between them.
Figure 4:
Figure 5:

The present method uses a device, shown generally in the context of use in FIG. 1 and by itself in FIG. 2 and which device if generally referred to by reference number 10 that includes two opposing handles 14, 18, joined by a transmission bar 22. Transmission bar 22 transmits forces applied from one handle 14, 18, to the other. Those forces are applied by a patient 26 in attempting to sit up and to lower herself back to a supine position. In addition to transferring force, transmission bar 22 conveys information about the relative fatigue and stress of patient 26. Each handle 14, 18, is sufficiently large to be grasped with both hands by either patient 26 or a caregiver 30, and may be 26-31 cm long. Transmission bar 22 is a single strong element, axially joined to the two opposing handles 14, 18. Transmission bar 22 may be 88-92 cm long. If transmission bar 22 is a single element, it is centered between the ends of each handle 14, 18, in the form of a long letter H. Device 10 may alternatively be in the shape of a rectangle with the shorter sides forming handles 14, 18, and the longer sides comprising transmission bar 22. Device 10 may be made of tubular elements, such as metal or a rigid, sturdy plastic.

Transmission bar 22 has two functions. First, and most obviously, it allows 30 caregiver to provide resistance to handle 14 grasped by patient 26 so that patient 26 can pull herself up. Second, transmission bar 22 provides a way for caregiver 30 to interact with patient 26 by making adjustments in the pulling force applied to handle 18. For example, if patient 26 is attempting to pull herself into a seated position by pulling on handle 14 while caregiver 30 holds handle 18 of device 10 stationary, patient 26 may get to an angle with respect to the horizontal but be losing strength. Caregiver 30 can to sense this loss of strength and respond by starting to pull on handle 18 slowly so that patient 26 can still move to a greater angle despite loss of muscle strength.

This use of device 10 for this type of physical communication between patient 26 and caregiver 30 also applies when patient 26 has pulled herself to a sufficiently great angle with respect to the horizontal and is then lowering herself while caregiver 30 holds device 10 stationary. When patient 26 tires, caregiver 30 can move device 10 slowly toward patient 26 so that the effort required of patient 26 is lessened. By adjusting effort, caregiver 30 can enable patient 26 to do a few more repetitions in each session than a patient 26 can do on her own and thereby improve performance more rapidly over time The use of device 10 in the present method to provide feedback to caregiver 30 is an important aspect of the present invention. The feedback transmitted by device 10 is at the very least additional information to caregiver 30 from the patient 26 and may be a significant part of the effectiveness of its use. Furthermore, the fact that caregiver 30 is assisting patient 26 encourages patient 26 to stay committed to the effort. That mutual commitment to the rehabilitation of patient 26 is critical when a patent is so debilitated and would naturally be daunted and discouraged by the challenge of rehabilitating herself. A bedridden patient 26 may also be depressed and inclined to give up when faced with a long and difficult rehabilitation process. If, however, caregiver 30 is assisting and providing encouragement and reassurance in the use of device 10, patient 26 will be energized, will be willing to cooperate and will continue to try.

The present device 10 facilitates techniques to enable caregiver 30 to improve the strength and endurance of patient 26. These include the adjustment of the level of effort required by caregiver 30 based on patient 26's performance and the use of both concentric and eccentric muscle movements. Because fatigue sets in quickly with those who are debilitated, optimizing each exercise is important, especially at the beginning of an exercise program. Using the techniques of the present method, patient 26 is enabled to do a little more in each repetition to see gains in strength that compound over time.

The combination of caregiver 30's participation and the particular techniques of the present method that involve both concentric and eccentric movements maximizes the chances of improvement. It is generally the case that over 80% of people who are generally healthy and who join a gym planning to get into shape will not be working out a year later; the failure rate for those who are bedridden and who are left to themselves to exercise as best they can is likely to be even higher. Accordingly, even a modest reduction in failure rate would be welcomed.

A bedridden patient 26 begins this exercise when caregiver 30 moves to the foot of patient 26's bed 28 and stands between its two spaced-apart corners, and patient 26 is lying on a bed 28. Caregiver 30, grasping handle 18 of one end of device 10 with both hands, extends an opposing handle 14 of device 10 toward patient 26 so that opposing handle 14 is no more than an arm's length away from patient 26. Patient 26 then reaches out and grasps handle 14 with both hands and begins to pull on handle 14, using it to try to sit up while bending at the waste, as caregiver 30 provides resistance against movement of device 10 until patient 26 either sits up or gets to a point where she cannot pull herself any higher. If the latter occurs, caregiver 30 may then slowly move device 10 closer to herself so that patient 26, still gripping it, is assisted in obtaining a seated position.

Next, while caregiver 30 continues to provide resistance against movement of device 10, patient 26 slowly lowers herself to a supine position onto bed 28. This sequence may be repeated.

Next caregiver 30 may take a step or two toward the side of bed 28 from the center of the foot of bed 28 and repeat the foregoing steps at this angle to work a different part of the patient 26's core muscles necessary for patient 26 to be able to roll left and right in bed, or to come to sit on the bedside. Caregiver 30 may then take a step or two to the opposing corner of bed 28 to work core muscles on the patient 26's other side. This process is repeated as long as patient 26 tolerates the effort. It is important to work toward a fuller range of motion, that is, with patient 26 seated upright and with less assistance by caregiver 30 but to do so gradually and to lower herself slowly to strengthen core muscles by eccentric motion. If necessary, brief rest between each repetition may be required.

In addition, for patients suffering from dysphagia, the patient can be instructed to cough while performing any of the above exercises.

Ideally, this exercise session should be repeated several times during the day. As core strength returns, the number of repetitions may be increased and then the angles at which caregiver 30 stands can be increased.

The present method may also be used as a complement to speech therapy. While performing the exercises designed to rehabilitate or maintain core strength, the patient may be encouraged to perform laryngeal exercises and vocal cord exercises, such as the pitch slide (or glide), to maintain swallowing safety and potentially address phonation issues by generally exercise the larynx, so as to maintain control over vocal modulation, intonation, and inflection Those familiar with physical, occupational, and speech therapy, particularly of those who have been in recovery for a long time and bedridden much of that time, will appreciate that many substitutions and modification in embodiments just described without departing from the spirit and scope of the present invention, which is defined by the present invention.

What is claimed is:

1. A method for using a device by a caregiver to rehabilitate a chronically bedridden patient, said patient lying in a supine position on a bed having a foot defined by two spaced apart corners, said device comprising a pair of opposing handles connected by a transmission bar, said method comprising the steps of:
   (a) moving, by said caregiver, to the foot of a bed between said two spaced-apart corners, where a chronically bedridden patient is tying in said supine position;
   (b) grasping, by said caregiver, a handle of said pair of opposing handles of said device with both hands;
   (c) extending, by said caregiver, an opposing handle of said device toward said patient so that said opposing handle is an arm's length away from said patient;
   (d) grasping, by said patient, said opposing handle with both hands;
   (e) pulling on said opposing handle, by said patient, while said patient moves from said supine position to a seated position by bending at the waist, while said caregiver holds said device stationary, and provides resistance against movement of said device and said caregiver senses a level of fatigue and stress of said patient, until said patient cannot pull closer to said opposing handle; and
   (f) while said caregiver continues to hold said device stationary and provides resistance against movement of said device, said patient slowly lowers back to said supine position.

2. The method of claim 1, further comprising the step of pulling on said handle, by said caregiver, when sensing said level of effort, fatigue and stress of said patient, to the extent needed to help said patient pull to a greater angle.

3. The method of claim 2, wherein said caregiver, when sensing said level of fatigue and stress, pulls on said handle by backing away from said bed.

4. The method of claim 2, wherein said caregiver, when sensing said patient cannot pull to a seated position, pulls on said handle.

5. The method as recited in claim 1, further comprising the step of performing, by said patient when performing steps (e) and (f), laryngeal exercises.

6. The method as recited in claim 5, wherein said vocal exercises are pitch glides.

7. The method as recited in claim 1, further comprising the step of moving, by said caregiver, to a first corner of said two corners before extending said opposing end of said device.

8. The method as recited in claim 1, further comprising the step of moving, by said caregiver, away from said bed, as said patient is pulling on said opposing end of said device.

9. The method of claim 1, wherein said caregiver instructs said patient to cough when said patient is moving between said supine position and said seated position.

10. A method for using a device by a caregiver to rehabilitate a chronically bedridden patient, said patient lying in a supine position on a bed having a foot defined by two spaced apart corners, said device comprising a pair of opposing handles connected by a transmission bar, said method comprising the steps of:
    (a) moving, by said caregiver, to the foot of a bed in which a chronically bedridden patient is lying;

(b) grasping, by said caregiver, a handle of said pair of opposing handles of said device with both hands;
(c) extending, by said caregiver, an opposing handle of said device toward said patient so that said opposing handle is an arm's length away from said patient;
(d) grasping, by said patient lying supine, said opposing handle with both hands;
(e) pulling on said opposing handle, by said patient, while said patient pulls from said supine position to a seated position by bending at the waist, while said caregiver holds said device stationary, providing resistance against movement of said device and sensing fatigue and stress of said patient, until said patient cannot pull closer to said opposing handle;
(f) while said caregiver continues to hold said device stationary and provides resistance against movement of said device, slowly lowering, by said patient, onto said bed back to said supine position; and
(g) performing, by said patient, laryngeal exercises.

11. The method as recited in claim 10, wherein said laryngeal exercises are pitch glides.

* * * * *